United States Patent
Chang et al.

(10) Patent No.: US 6,734,880 B2
(45) Date of Patent: *May 11, 2004

(54) USER INTERFACE FOR A MEDICAL INFORMATICS SYSTEMS

(75) Inventors: Paul Joseph Chang, Allison Park, PA (US); Bradford V. Hebert, Piedmont, CA (US); Benjamin J. McCurtain, San Francisco, CA (US)

(73) Assignees: Stentor, Inc., Brisbane, CA (US); University of Pittsburgh of the Commonwealth Sytem of Higher Education, Pittsburgh, PA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/449,115

(22) Filed: Nov. 24, 1999

(65) Prior Publication Data

US 2002/0109735 A1 Aug. 15, 2002

(51) Int. Cl.⁷ .................................................. G09G 5/00
(52) U.S. Cl. ..................... 345/738; 345/735; 345/730; 345/732; 345/800; 345/786; 345/788
(58) Field of Search .............................. 345/716, 738, 345/730, 732, 769, 650, 660, 670, 671, 661, 672, 684, 800, 801, 786, 788

(56) References Cited

U.S. PATENT DOCUMENTS

| | | | |
|---|---|---|---|
| 5,431,161 A | * 7/1995 | Ryals et al. | 600/425 |
| 5,452,416 A | * 9/1995 | Hilton et al. | 345/783 |
| 5,542,003 A | 7/1996 | Wofford | |
| 5,680,152 A | 10/1997 | Bricklin | |
| 5,954,650 A | * 9/1999 | Saito et al. | 600/425 |
| 5,986,662 A | * 11/1999 | Argiro et al. | 345/424 |
| 5,987,345 A | 11/1999 | Engelmann et al. | |
| 6,177,937 B1 | * 1/2001 | Stockham et al. | 345/807 |
| 6,269,379 B1 | * 7/2001 | Hiyama et al. | 707/104 |

FOREIGN PATENT DOCUMENTS

| | | |
|---|---|---|
| JP | 10225441 | 8/1998 |
| JP | 11290279 | 10/1999 |

* cited by examiner

*Primary Examiner*—Ba Huynh
(74) *Attorney, Agent, or Firm*—Stattler Johansen & Adeli, LLP

(57) ABSTRACT

A user interface for a medical informatics system, which permits a physician to work with digitized medical images in a manner that the physician is accustomed to working with traditional analog film, is disclosed. The user interface includes a through a patient browser view to provide the ability to select studies, which consist of medical images and series, for patients. After selecting the studies, the user, through a patient canvas view, may then organize the studies as well as the images/series within the studies, including resizing the studies and the images/series within a study. The user may also pan and zoom images to view portions of an image at various resolutions. Furthermore, the user of the user interface may analyze the image by selecting to view the image in detail in a large floating window.

27 Claims, 9 Drawing Sheets

USER INTERFACE FOR A MEDICAL INFORMATICS SYSTEMS

BACKGROUND OF THE INVENTION

1. Field of the Invention

The present invention is directed toward the field of medical informatics, and more particularly toward a user interface for a medical informatics system.

2. Art Background

Radiology equipment (e.g., CT scanners, MRI scanners, X-Ray etc.) is in wide spread use as diagnostic tools in hospitals today. Traditionally, radiology departments utilize equipment, such as X-Ray machines, that generate images on film. Typically, when collecting information from a diagnostic tool, several medical images are generated for subsequent analysis and diagnosis of the patient's medical condition. This collection of medical images may be referred to as a "study." For example, a study from an X-Ray machine may consist of a number of X-Rays taken from different perspectives of the target area. It is the totality of the study that the physician uses to make a diagnosis of the patient.

It has become more common in the medical field for images to be stored, distributed, and viewed in digital form using computer technology. Currently, Picture Archival and Communication Systems or PACS have been in widespread use. In a typical PACS application, image data obtained by imaging equipment such as CT scanners or MRI scanners are stored in the form of computer data files. The size of a data file for an image varies depending on the size and resolution of the image. For example, a typical image file for a diagnostic-quality chest X-ray is on the order of 10 megabytes (MB). The image data files are usually formatted in a "standard" or widely accepted format. In the medical field, one widely used image format is known as DICOM. The DICOM image data files are distributed over computer networks to specialized viewing stations capable of converting the image data to high-resolution images on a CRT display.

The digitized medical images potentially provide to the medical community advancements due to the ability to electronically store, transfer and view digitized images over geographically disparate areas. However, prior art systems for viewing the digital data do not comport with how physicians traditionally operate. Physicians have become accustomed to working with analog film. First, to conduct a diagnoses using traditional film, the physician chooses the films for a patient that will aid in the analysis of the patient's condition. From the selected films, the physician organizes the films in a manner suitable to conduct the analysis and subsequent diagnoses. Specifically, the film is placed on a light board for viewing. The light board projects light through the film so that the physician may read the image imposed on the film. Prior to analyzing a study, a physician may organize the physical sheets of film on the light board in a manner suitable for conducting the analysis. It may be advantageous for a physician to place, on the light board, two sheets of film next to one another in order to analyze a condition relative to the two films. For example, the first film may comprise data taken at an earlier date, whereas the second film may contain data recently obtained. By placing the films side-by-side, the physician may analyze how a particular condition has changed over time.

Prior art systems for viewing digitized medical images do not provide a means to operate in a manner in which physicians work. As illustrated by the above example, using these prior art systems, a physician is not permitted to effectively organize medical images in a manner in which physicians may organize traditional analog films. Accordingly, it is desirable to develop a user interface for a medical informatics system that emulates the way a physician works by providing maximum flexibility for the physician to select, organize, navigate and subsequently analyze medical images. Furthermore, prior art systems for viewing digitized medical images display static images, in that the user is not permitted to navigate (i.e., pan or zoom the original image). Accordingly, it is also desirable to generate a system that permits "dynamic" interaction with medical images to provide the physician with maximum flexibility to interact with the image.

SUMMARY OF THE INVENTION

A user interface for a medical informatics system permits a physician to work with digitized medical images in a manner that the physician is accustomed to working with traditional analog film. The user interface provides the user to ability to select studies, which consist of medical images and series, for patients. In one embodiment, the user selects studies on the user interface through a patient browser view. After selecting the studies, the user may then organize the studies as well as the images/series within the studies, including resizing the studies and the images/series within a study. The user may also navigate around the images/series. Specifically, the user has the ability to pan and zoom images to view portions of an image at various resolutions. Furthermore, the user of the user interface may analyze the image by selecting to view the image in detail in a large floating window. In one embodiment, the organization, navigation, and analysis of studies and images/series are performed through a patient canvas view.

In one embodiment, the patient canvas view is displayed in a standard orientation such that each horizontal scroll bar contains a study. For this embodiment, each study displayed on the patient canvas view is broken out left to right into one or more series for CT/MR and one or more images for CD/DR. The user, using a horizontal scroll bar is permitted to scroll left and right to display the series/images contained within the study. Multiple studies are laid out from top to bottom on the patient canvas view. A single vertical scroll bar is provided to permit the user to scroll, in a vertical direction (i.e., from top to bottom), to display the multiple studies. Using the user interface, the user may organize studies by re-arranging the relative vertical positions among the studies. Thus, the studies (i.e., the window encompassing the studies) may be re-sized to any user-desired size. The user may also use the features of the patient canvas view to organize images, within a study, by re-arranging the relative horizontal positions among the images/series within a study via a drag and drop operation.

BRIEF DESCRIPTION OF THE DRAWINGS

FIG. 8b illustrates level three and level four decompositions for the 4K×4K source image of FIG. 8a.

DETAILED DESCRIPTION

Figure 1:
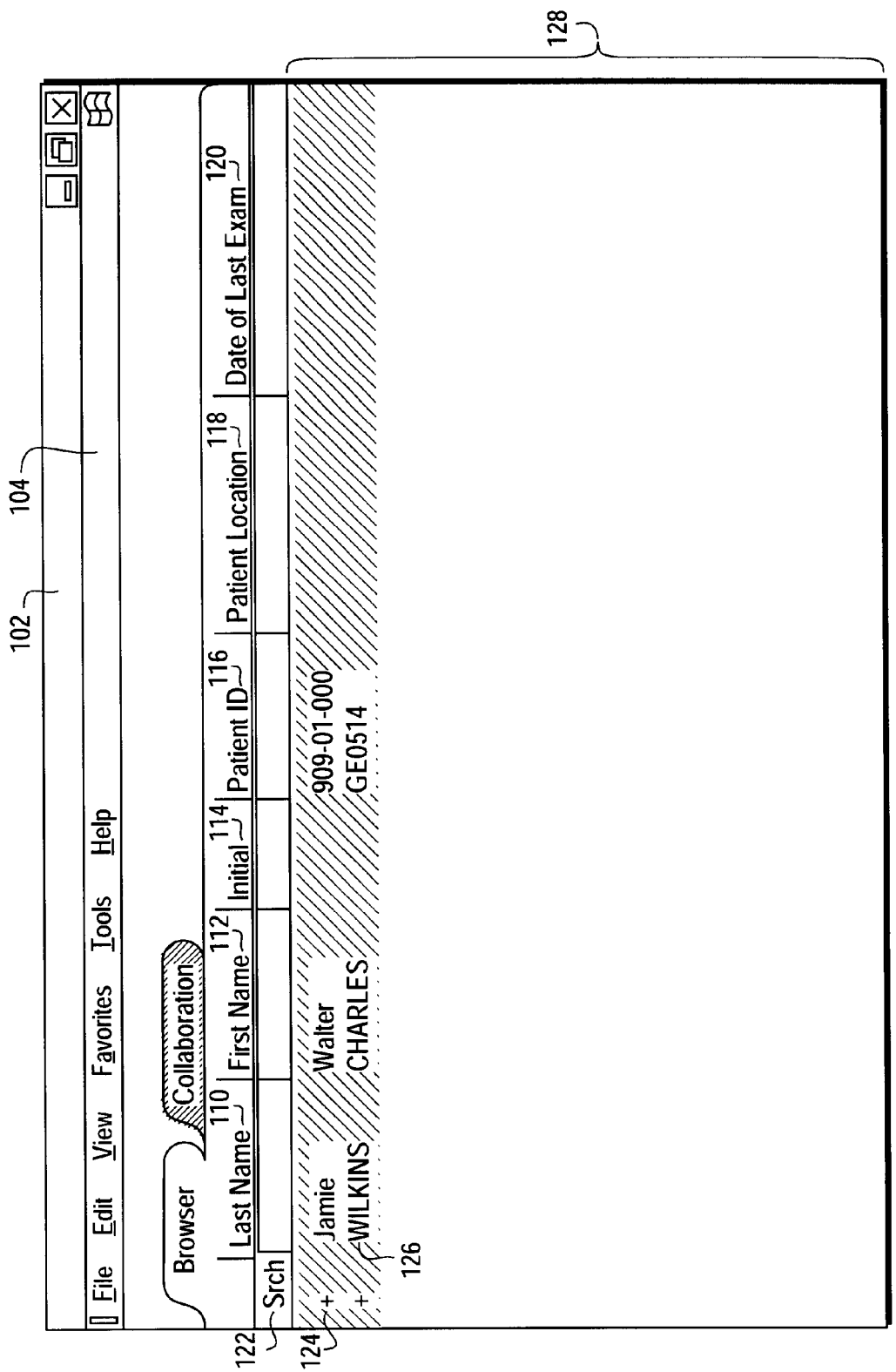
FIG. 1 illustrates one embodiment for an initial patient browser view.

The user interface of the medical informatics system provides a ubiquitous viewing environment for fast and simple access to medical images across the enterprise. The user interface may be operated by a physician in manner in which physicians are accustomed to working with traditional analog film. First, the user of the medical informatics system may select studies, which consist of medical images/series, for patients. In one embodiment, this functionality is provided through a patient browser view. The user may then organize the studies as well as the images/series within the studies, including resizing the studies and the images/series within a study. The user may also navigate around the images/series. Specifically, the user has the ability to pan and zoom images to view portions of an image at various resolutions. Furthermore, the user of the user interface may analyze the image by selecting to view the image in detail in a large floating window. In one embodiment, the organization, navigation, and analysis of studies and images/series are performed through a patient canvas view. Accordingly, the user interface of the present invention emulates the way a physician works with medical images by providing full capabilities to select, organize, navigate and analyze medical information.

In one embodiment, the user interface consists of primarily a single window interface. However, additional floating windows are generated, when appropriate, to provide detailed image viewing. For the single window interface embodiment, tabs are presented to the user to permit the user to navigate between a patient browser view and one or more patient canvas views. In general, the patient browser view permits the user to select studies for one or more patients. A study, specific to a patient, comprises images obtained from a diagnostic tool, and in some cases, additional information (e.g., medical report) to augment the image data. The studies define the repository of medical images that may be used during the session. The patient canvas view provides a screen surface area for the organization, navigation and analysis of the patient medical information selected.

In one embodiment, the user interface presents the user with a simple login window. Using this login window, the user may enter a user name and password. If the user is successfully authenticated by the server (e.g., image server 720, FIG. 7), then the main window of the client computer is displayed with the patient browser tab selected.

In one embodiment, the user interface operates as a plug-in with an Internet browser application, such as Microsoft Internet Explorer or Netscape Navigator. In one embodiment, the user interface comprises, in part, executable software configured as a Microsoft® ActiveX Control. For this embodiment, the ActiveX Control is a "plug-in" to a Web browser application. The Internet browser application includes a title bar (e.g., title bar 102, FIG. 1) including controls to minimize, maximize and close the browser application, as well as a tool bar (e.g., tool bar 104, FIG. 1). Although the user interface is shown herein as an Internet browser plug-in, the user interface may operate independent of other application programs without deviating from the spirit or scope of the invention.

Patient Browser View for Selecting Studies:

FIG. 1 illustrates one embodiment for an initial patient browser view. For this embodiment, following user login, the user interface opens and displays a patient browser tab, labeled 106 on FIG. 1. In one embodiment, the user interface 100 contains search capabilities to permit a user to locate and select medical information for one or more patients. For this feature, the user interface 100 contains, as part of the patient browser tab view, controls and entry boxes (122) to allow searching for patients and studies. Specifically, entry boxes for searching include: patient's name 110, patient ID 116, patient location 118, and date of last exam 120. The user interface 100 also permits submission of predefined queries for the fields: physician, patient location, physician group, and body part. These predefined queries are stored as part of a user profile. The physician group is a class that groups different types of physicians (e.g., neurology, orthopedic, oncology, etc.). The physician groups may be assigned by an administrator of the medical informatics system. If the predefined query occurs as part of the user login process, then the initial state of the patient browser displays the results of that query. Alternatively, if a login query is not found or available, then there is no content in the patient list display area.

In general, the patient browser list view 100 displays a list of patients and their corresponding studies. Information on patients and their studies is displayed in the area labeled 128 in the user interface window 100. The example display of the FIG. 1 displays, in a patient list display area, information for two patients, Jamie Walter 124 and Charles Wilkins 126. A patient ID, corresponding to the patient's name, is also displayed. For this embodiment, the list of studies only indicates the specific study, and does not indicate the series or image contained in that study. As shown in FIG. 1, the information displayed for each patient includes: last name 110, first name 112, middle initial 114, patient ID 116, patient location 118, and date of last exam 120 (derived from the most recent study). In addition, the user may sort the list of patients by last name, patient location, and date of last exam.

Figure 2:
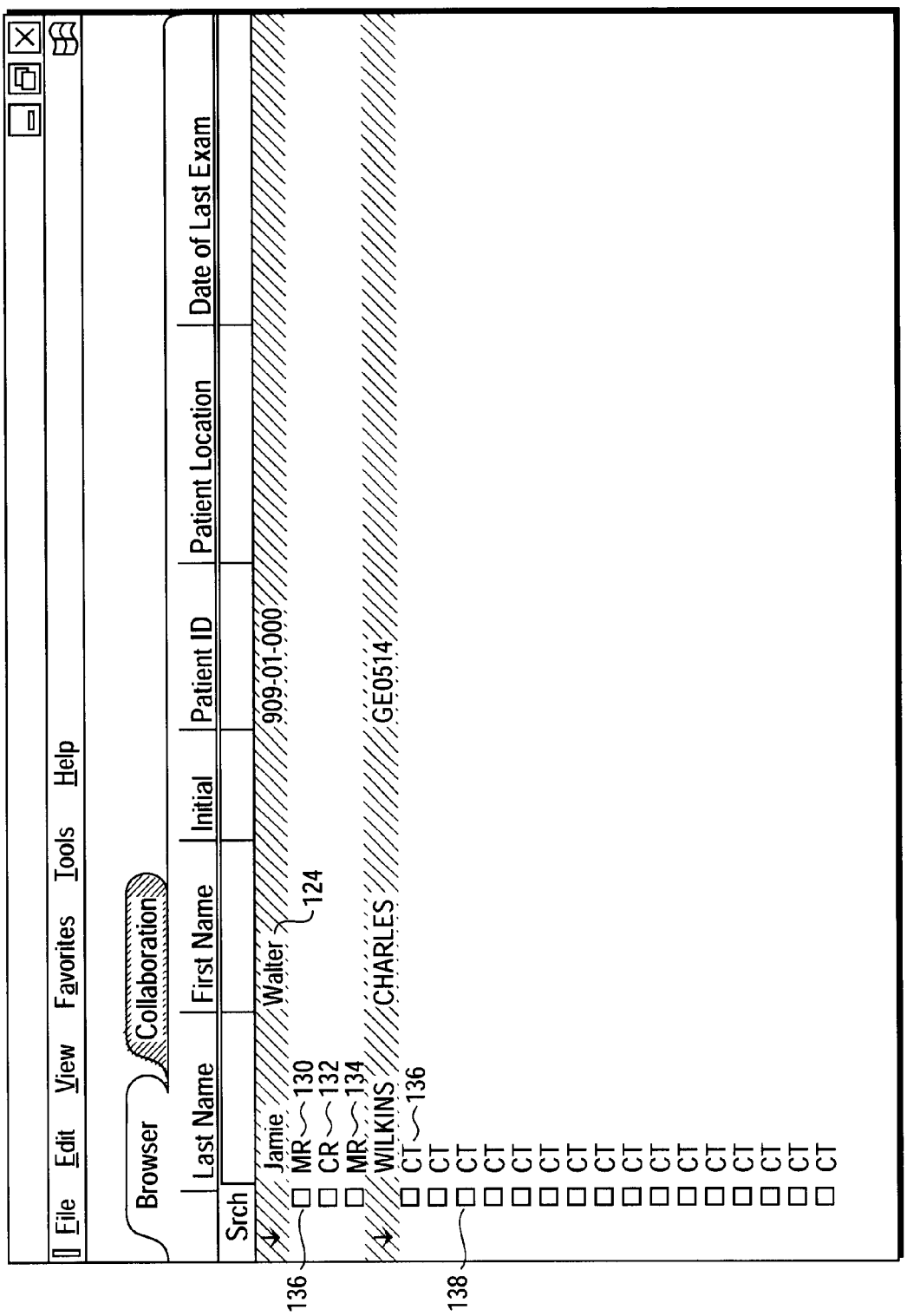
FIG. 2 illustrates an example patient browser view with a plurality of the studies for each patient.

FIG. 2 illustrates an example patient browser view with a plurality of the studies for each patient. To obtain the patient browser view of FIG. 2 from the patient browser view of FIG. 1, the user, using a cursor control device, "clicks" on a patient name line (e.g., patient name line 124 for Jamie Walter and patient name line 126 for Charles Wilkins), and the studies available for that patient are displayed. As shown in FIG. 2, a tree paradigm is used to display the studies beneath the patient title bars 124 and 126. For the hierarchical patient study display of the FIG. 2, the display line for each study includes: a check box to indicate selection status, modality, study description, accession number, and exam date. Specifically, the example of FIG. 2 shows, for the patient "Walter Jamie", the studies labeled 130, 132 and 134 on FIG. 2. The abbreviation "MR" connotes magnetic resonance, and the abbreviation "CR" connotes conventional radiography (e.g., an X-Ray). For the patient "Charles Wilkins", a plurality of CT studies are revealed.

Figure 3:
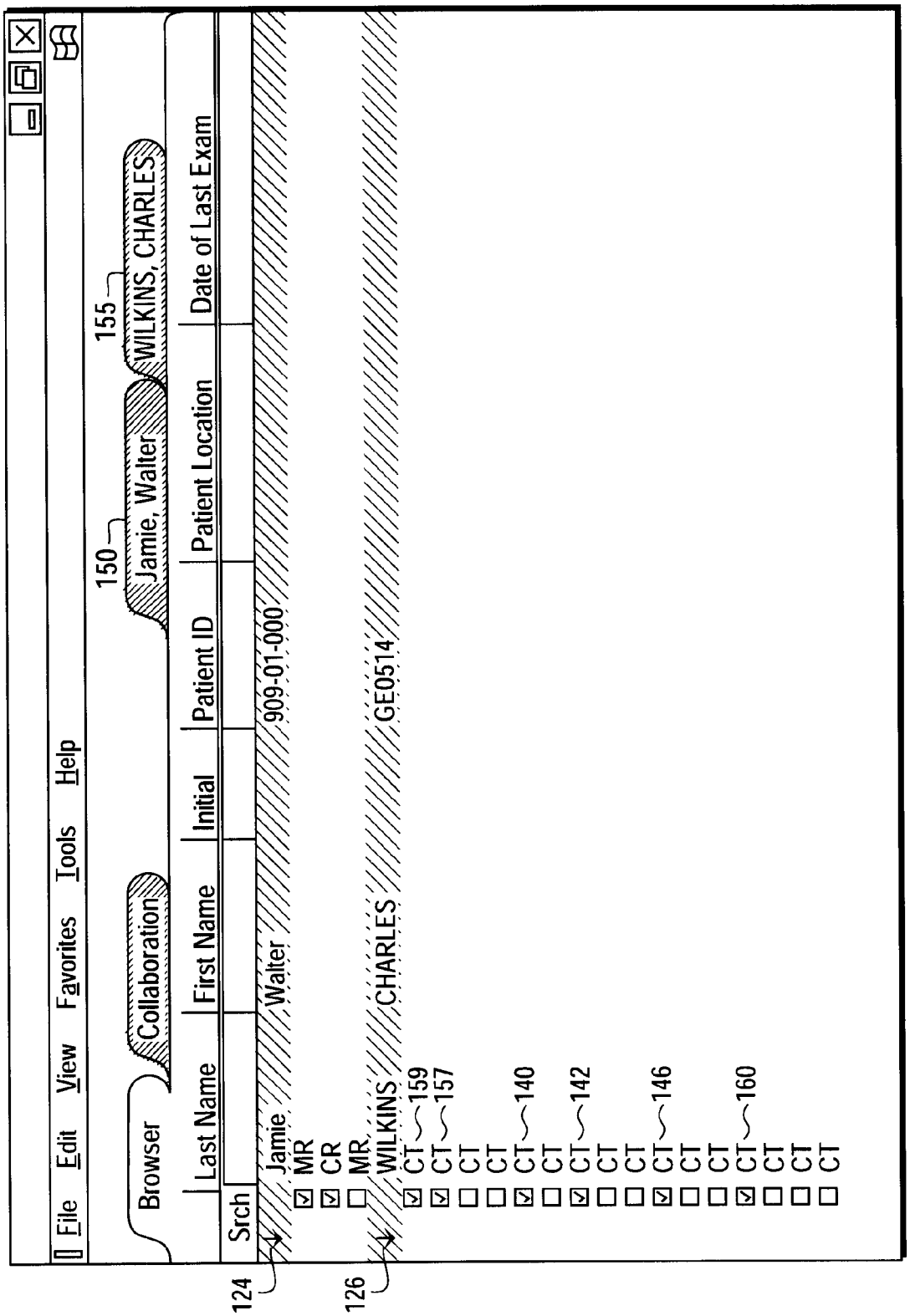
FIG. 3 illustrates an example display of a patient browser view that includes selection of patient studies.

If the user clicks, using a cursor control device, to select a study, then the selection check mark in the check boxes 136 and 138 are toggled. FIG. 3 illustrates an example display of a patient browser view that includes selection of patient studies. For this example, the user selected, for the patient "Charles Wilkins", CT studies 140, 142, 146, 157, 159 and 160. The selection of the studies are indicated by the check mark in the check box adjacent to the study description (e.g., CT). This selection response adds and or subtracts studies from the current selection for subsequent display in the patient canvas view. In other embodiments, additional user interface features for the patient browser view permit ease of selecting and deselecting studies. For example, the key strokes "shift—click" executed by the user selects a contiguous range of studies. The key strokes "control—click" deselects all other studies and selects the single study.

As study selections are made by the user from the patient browser view, the user interface creates tabs for each patient that has at least one study selected. For the example shown in FIG. 3, patient tabs 150 and 155 are displayed for the patients "Walter Jamie" and "Charles Wilkins", respectively. The tabs are created on a per patient basis, one tab for each patient with selected studies. For this embodiment, the tabs are displayed from left to right in an order dictated by the current sort order. The example of FIG. 3 shows sorting of the patient's last name in alphabetical order. The user may move to the patient canvas view (described below) for that patient by selecting the corresponding tab. As a shortcut, if the user "double clicks" on a patient's name (e.g., line 126 for Charles Wilkins and line 124 for Jamie Walter), a canvas tab is created for the patient, and that tab is displayed similar to tabs 150 and 155 on FIG. 3. As a shortcut to adding the canvas tab for the patient and selecting all studies for display on the patient canvas view, the user "double-clicks" on a study in the list. If all studies are selected during a double-click, then each of the selected studies are displayed within the canvas view.

Figure 4:
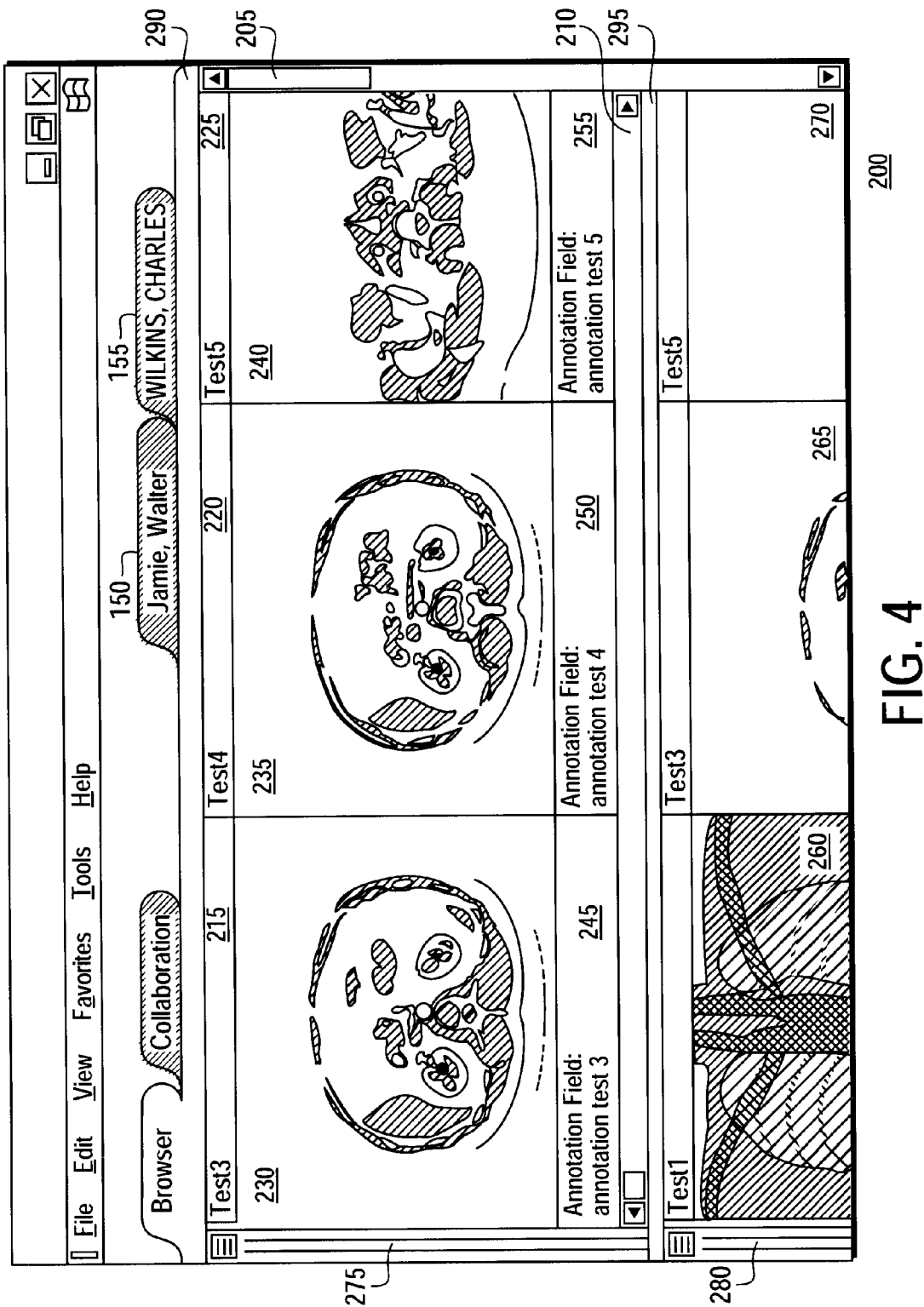
FIG. 4 illustrates an example patient canvas view in accordance with one embodiment of the present invention.

Patient Canvas View for Organization of Studies and Images:

In general, the patient canvas view of the user interface permits a user to organize, navigate, and analyze images/series in the studies selected. FIG. 4 illustrates an example patient canvas view in accordance with one embodiment of the present invention. A patient canvas view 200 includes a plurality of studies for the selected patient, "Jamie, Walter." As shown in FIG. 4, the patient tab, labeled 150 for "Jamie, Walter" is highlighted. Each tab displayed has a corresponding patient canvas view. Thus, another patient canvas view exists for the patient "Charles Wilkins."

The area beneath the displayed tabs is the primary display area for the studies and series/images. For the example of FIG. 4, two studies, arranged vertically on the screen, are shown. In one embodiment, selected studies are automatically laid out from top to bottom on the patient canvas view. Each study is broken out left to right into one or more series for CT/MR and one or more images for CD/DR. In the example of FIG. 4, the first or top study includes the series of images labeled 230, 235 and 240 on FIG. 4. The second study, displayed on the bottom of the patient canvas view, currently displays the three images: 260, 265, and 270.

In one embodiment, the patient canvas view is displayed in a standard orientation such that each horizontal scroll bar (scroll bar 110 for the top study) contains a study. The user, using the horizontal scroll bar (e.g., horizontal scroll bar 110), is permitted to scroll left and right to display the series/images contained within the study. Also, a single vertical scroll bar (e.g., vertical scroll bar 205 on FIG. 4) is provided to permit the user to scroll, in a vertical direction (i.e., from top to bottom), to display multiple studies. Furthermore, the height of each study may be varied within the patient canvas view. To accomplish this operation, the user, using a cursor control device, places the cursor on a horizontal grab bar on the study (e.g., bar 290 for the top study and bar 295 for the bottom study), and resizes the study to the appropriate height. Using this technique, the studies (i.e., the window encompassing the studies), may be resized.

Using the user interface, the user may organize studies by re-arranging the relative vertical positions among the studies. The user may also use the features of the patient canvas view to organize images, within a study, by rearranging the relative horizontal positions among the images/series within a study. In one embodiment, these organization operations are executed via a drag and drop operation. As is well known, in a drag and drop operation, the user "selects" a series/image or study, and drags the series/image or study to the destination location. When the image is located at the destination location, the user releases the series/image or study to complete the drag and drop operation. A control "hot area" at the left side of each study row is displayed to provide a handle for the user to grab the study in the drag and drop operation. The study "handle" is labeled 275 for the top study and is labeled 280 for the bottom study of the FIG. 4. The series (CT/MR) and images (CR/DR) may also be re-arranged within a study (i.e., re-arrange relative horizontal positions) using the drag and drop operation. For this operation, the user may "grab" an image or series using the title bar or annotation area, such as title bar 220 for series 235 on FIG. 4. The drag and drop operation provides maximum flexibility for the user to arrange the patient canvas view in any manner desired by the user.

The position of studies and images displayed on the patient canvas view may also be arranged by user execution of a cut and paste operation. As is well-known for a general cut and paste operation, the user selects the study (e.g., using the cursor control device or entering a keystroke sequence), executes the cut operation with the appropriate keystroke, re-positions the cursor with the cursor control device in the new destination location, and executes the "paste" command.

In one embodiment, a rule set is applied to analyze a study of series/images displayed in a single row to determine the proper height for the row. Using this technique, row heights are selected based on the nearest optimal representation. The default target row height is 320 pixels. The actual row height is determined by analyzing the row contents (i.e., series/images) so that unnecessary space is eliminated. In another embodiment, the row height is saved as a user preference, and a target row height is used to display studies for that user. In other embodiments, the target row height is determined from the user's screen size or window resolution.

The patient browser view on the user interface provides the functionality to "clone" an image. To this end, a user may copy an image or series, and paste the image or series in a different location. For the example shown in FIG. 4, the user may copy, through a standard copy operation, image 260 in the second study (i.e., the bottom study), and paste the image to the right of image 265. In other embodiments, the user may copy an image in one study (e.g., the bottom study), and paste the image into a different study (e.g., the first or top study). The result of this operation is shown on the display of FIG. 5, starting with the display of FIG. 4, with image 260 appearing in both the first and second studies.

Figure 5:
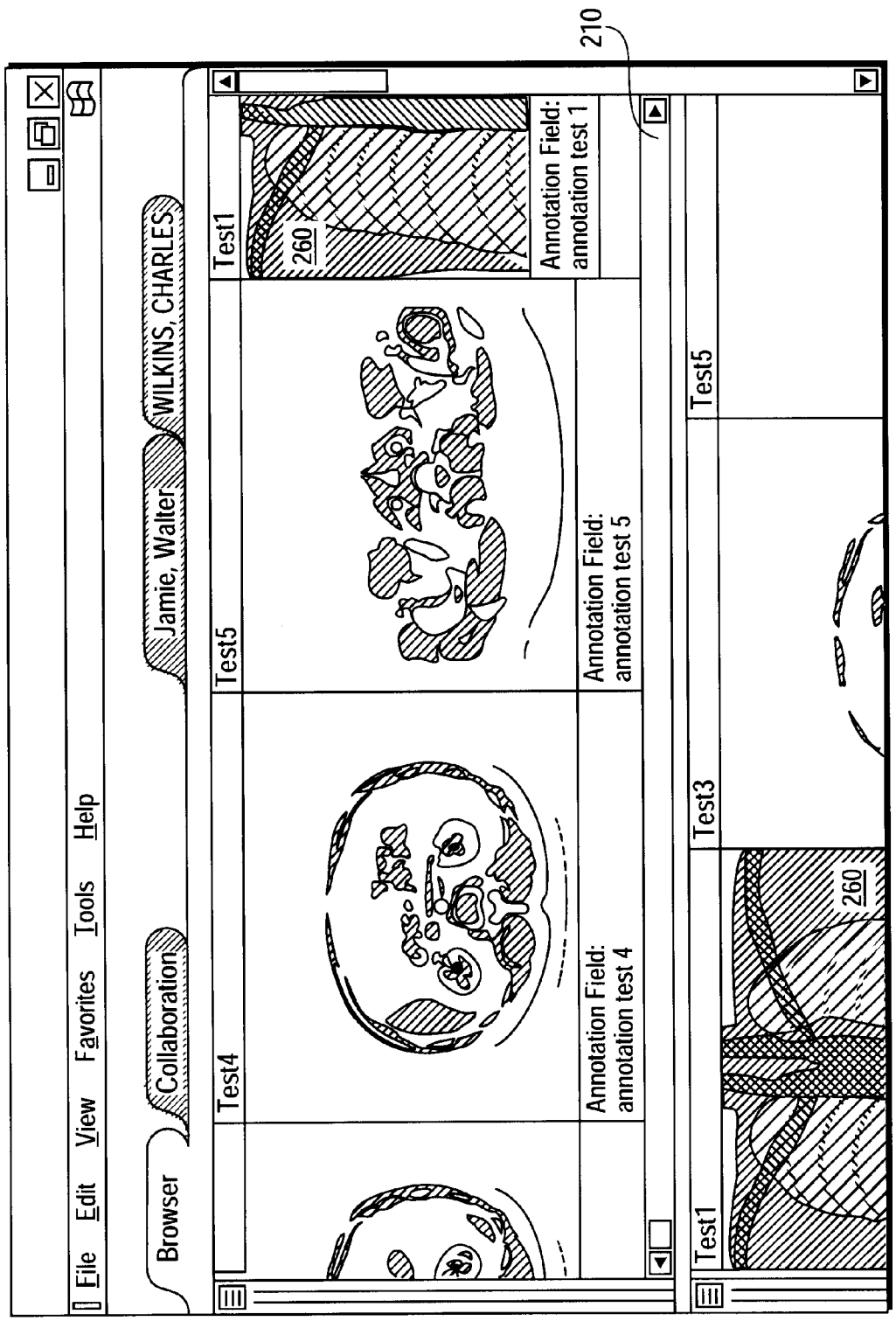
FIG. 5 illustrates a user operation to scroll images within a study.

FIG. 5 illustrates a user operation to scroll images within a study. To view additional images contained in the first study shown in FIG. 4, the user, utilizing scroll bar 210, scrolls through the images/series contained within the study. FIG. 5 shows a different view from the study of FIG. 4 subsequent to a user operation to scroll the images/series from right to left.

Figure 6:
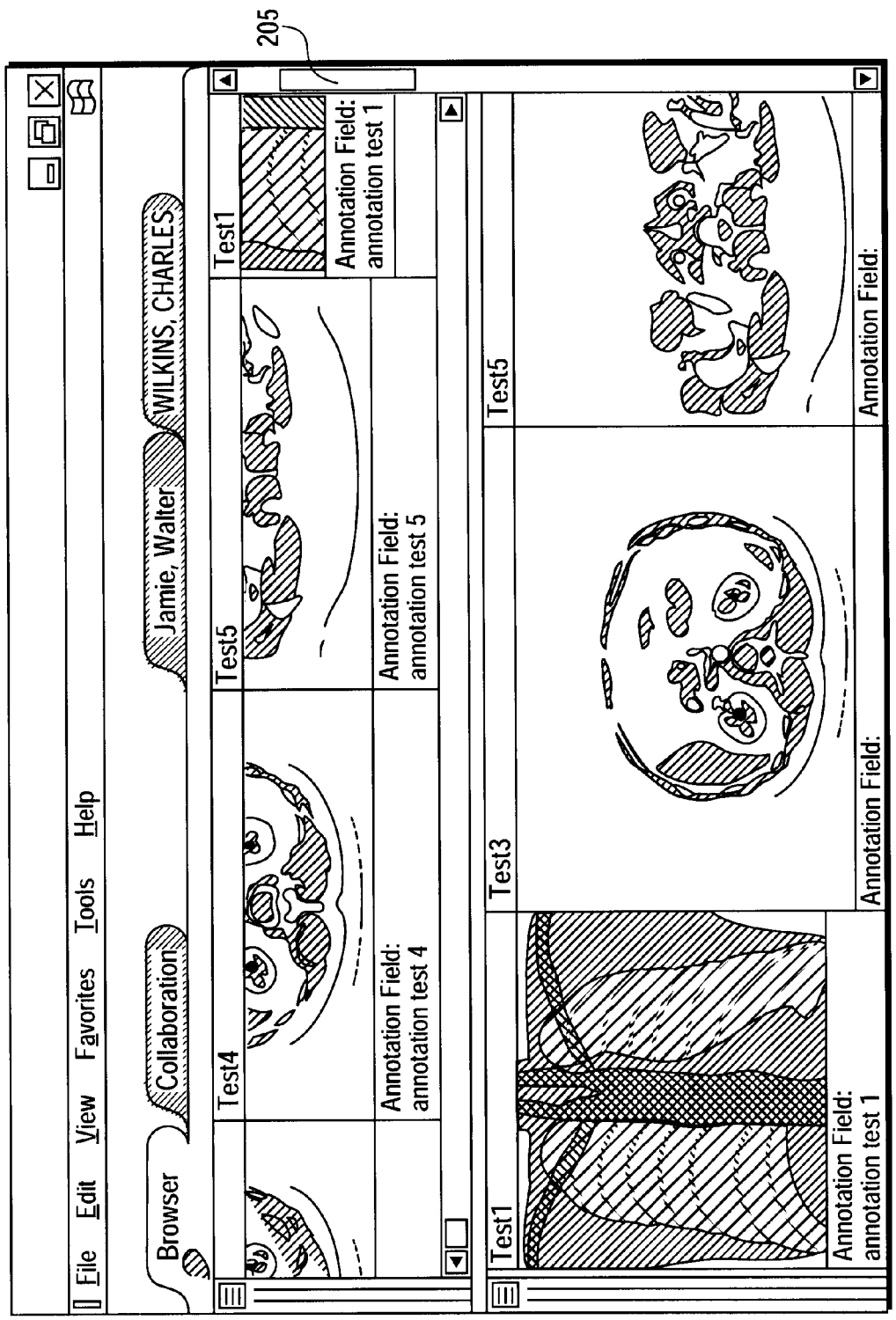
FIG. 6 illustrates the patient canvas view subsequent to a user operation that scrolls among studies.

FIG. 6 illustrates a user operation to scroll among studies. FIG. 6 illustrates the patient canvas view subsequent to a user operation that scrolls among studies. Specifically, for this example, the user, utilizing the scroll bar 205, scrolls, in a vertical direction (e.g., from bottom to top), the top and bottom studies to view more of the bottom study (and subsequently less of the top study).

In one embodiment, each series/image displayed within a study includes control points and annotation information. The control points and annotation information may be implemented similar to a standard window in a user interface. For example, the study "date and time" may be displayed at the top of the image, and the study and series descriptive information may be displayed below the image. For the example of FIG. 4, the image 230 of the top study includes, as a control point, the bar with the text "test 3", labeled 215, and an annotation field 245 entitled "annotation test 3." The annotation field may include any type of information used to describe the image, including image frame and canvas row frame information. In addition, for floating windows (described below), annotation information such as patient name and date of study may be displayed.

After a session, the selection and arrangement of studies and images/series are stored in a persistent datastore. When that user selects the same patient again, the patient browser view is restored to the previous display from the prior session.

Patient Canvas View for Navigation and Analysis of Images:

The patient canvas view of the user interface permits a user to fully "navigate" the image. Typically, medical images are large, and cannot be displayed at full resolution on a computer monitor. Thus, when displayed in small windows (e.g., image 235 in FIG. 4 displayed at approximately 320 pixels), only portions of the medical image are displayed at any one time. For example, a medical image consisting of a pixel resolution of 4K×4K cannot be displayed at full resolution on a monitor comprising a pixel resolution of 1024×768. Thus, only portions of the 4096× 4096 source image are displayed through the user interface at a given time. For example, the user interface may display, in a 512×512 window, the entire source image at a lower resolution (i.e., a thumbnail sketch of the image).

The images, displayed on the user interface, are "dynamic images." The images are dynamic because the user may fully manipulate each image to display different portions of the image (pan the original image) at different resolutions (zoom in and out). In one embodiment, a dynamic transfer syntax, described below, provides full functionality to allow the user to manipulate the image in any manner desired. Starting with the lower resolution "dynamic image", the user may zoom-in on a more specific portion of the image. Thereafter, the user may pan the image to view a different portion of the image at the higher resolution. Accordingly, through the pan and zoom functions, the user may navigate through the images.

In one embodiment, only portions of an image are displayed as the user continuously pans an image. The eye is only capable of perceiving a certain level of detail while pixels are moving during the pan operation. The user interface takes advantage of this fact and only uses a lower resolution version of the image during the pan operation. The lower resolution version provides adequate detail for user perception. When the continuous panning activity halts, additional details are supplied to the image to display the image at the desired resolution. This feature enhances performance of the medical informatics system in low network bandwidth implementations.

The patient canvas view on the user interface permits a user to link series within the canvas. With this feature, as a user scrolls through slices of a first series, the second series, linked to the first series, is also scrolled. The patient canvas view also permits linking of any image or series, including images and series displayed in floating windows. The user interface also permits a user to clone a series for display at different window widths and window levels ("WW/WL") (i.e., contrast and brightness, respectively). The user interface further permits a user to scroll a CT/MR series to a particular slice, and then link this series to another series for simultaneous cine. In addition, the patient canvas view maintains, for simultaneous cine between two series, the same anatomical position for both series, even if the series contains a different number of slices. For example, a first series may contain 100 slices within an anatomical position of a patient, and a second series may contain only 10 slices within the same anatomical position of the patient. For this example, the simultaneous cine feature displays 10 slices of the first series for every 1 slice of the second series. WW/WL acted upon any of the three display modes is inherited by subsequent display of that series or image during the current session. This includes larger windows created for a series or image. Multiple link channels are supported, as indicated by a number by a link icon and a drop down selection option at the point of linking. For this embodiment, the user may move through a single or link series with a scroll wheel on a cursor control device, pan and zoom around CR/DR images, and use the left button of the cursor control device to change WW/WL.

The patient canvas view of the user interface permits a user to fully "analyze" the image. For the analysis stage, the user interface of the present invention permits a user to create detailed views of selected images. In one embodiment, the user interface for the medical informatics system permits the user to generate large floating windows for detailed views. The detailed views permit a physician to analyze the image once the desired portion of the image is located in the navigation phase. For example, if the user navigates to a specific portion of a large image, the user may invoke the user interface to display the detailed portion of the image in a large floating window size to capture the full resolution of the specific portion. In one embodiment, to create a floating window, the user double-clicks on the image, using the cursor control device, and the image is displayed in the large floating window. In one embodiment, the full floating window consists of approximately 75 percent of the display area. For example, the floating window target height may be 640 pixels, as compared to the study scroll area target height of 320 pixels. For standard CT/MR, the display area may comprise a 512×512 pixel window.

Linked images and series may also be displayed in floating windows. In one embodiment for implementing this feature, the user double clicks on a linked image, or selects multiple series/images, to receive a display of a collage of those series/images, each displayed as a floating window. In this view, the user may cine through the series, as described above, linked or unlink two series, change the WW/WL with the right mouse button, or pan and zoom with a single or linked CT/DR images.

A double-click at the floating window level or zoom box control takes the user directly to the full screen display mode with the same image manipulation interactions. On a floating unlinked CT/MR series window, a double click cursor action by the user brings the images up to a nine-on-one tile mode. The nine-on-one tile mode displays images on top of one another. Under this scenario, the user may use the scroll wheel to move the tile images back and forth one page at a time. A left-hand button on the cursor control device permits the user to WW/WL upon all the displayed images, so as to maintain persistence while scrolling the pages. In one embodiment, for the nine-on-one tile mode, the size of each image within the window may comprise 256×256 pixels. In one embodiment, floating windows have basic intelligent layout properties, in that multiple floating windows stack using an offset of approximately 16 pixels to the right and 100 pixels down. As an additional feature, the floating windows have a button at the base of the window for prior image/series and next image/series control. Also, the floating windows have a link item menu available on the lower right corner of the image area, similar to the link button on the canvas. This allows shared pan zoom for plain images, shared cine for CT/MR series and shared page by page review for CT/MR series in tiled mode. Additionally, the user interface permits the user to toggle, using the cursor control device and keys, functionality between pan/zoom and slice navigation for CT/MR images.

In one embodiment, the user interface displays, in addition to image/series and studies, radiological reports to the left side of each study display area. The report area is associated with the study, and a scroll bar permits the user to scroll vertically to read the text contained in the report. In one embodiment, the report feature includes a "splitter" control bar so as to allow the user to adjust the horizontal display area of the report area to expand or contract the size. Example splitter control bars 275 and 280 are shown in FIG. 4.

Figure 7:
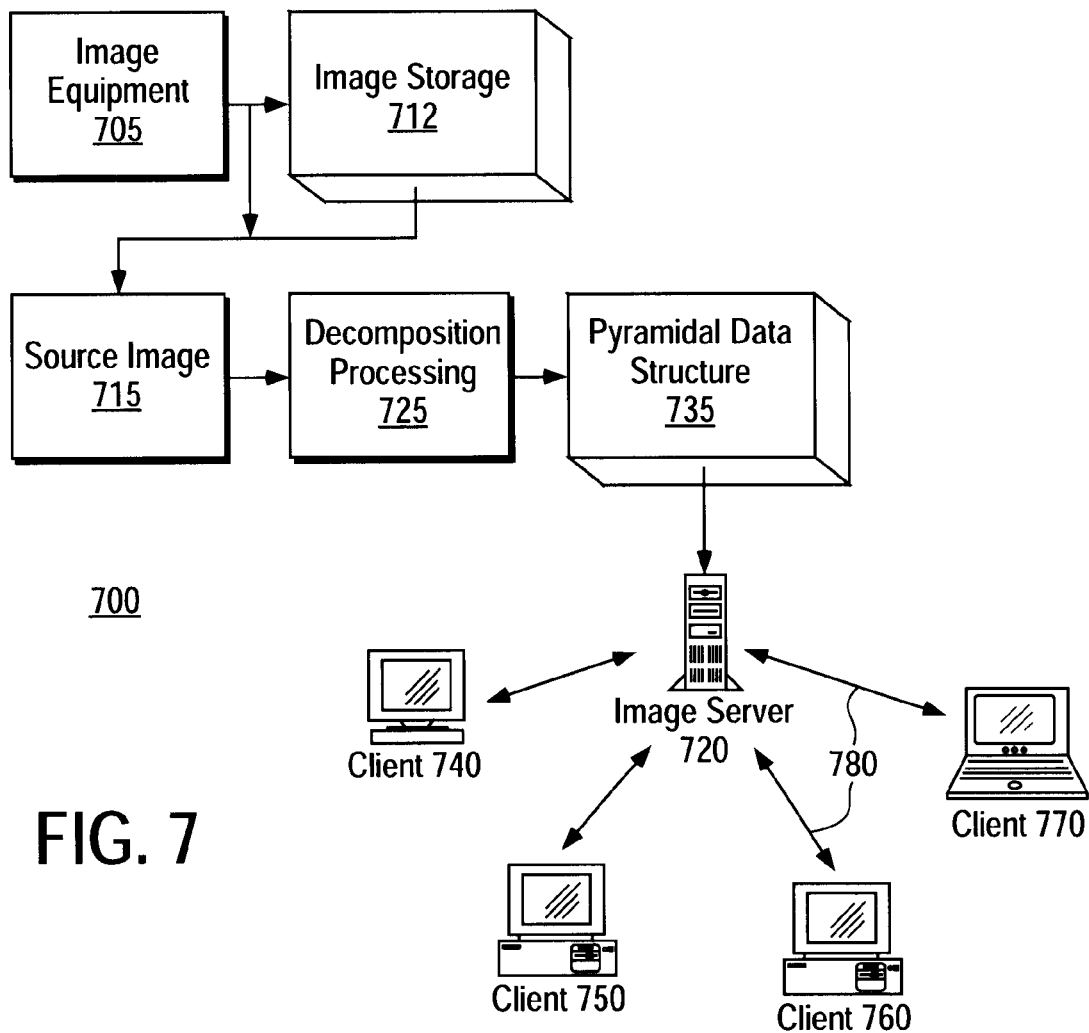
FIG. 7 illustrates one embodiment of a medical informatics system for use with the user interface of the present invention.

Medical Informatics System:

FIG. 7 illustrates one embodiment of a medical informatics system for use with the user interface of the present invention. In one embodiment, a medical informatics system employs dynamic transfer syntax. For this embodiment, medical informatics system 700 includes imaging equipment 705 to generate source images 715 for storage in electronic form in an image archive 712. The image archive 712 contains electronic storage components such as disk drives and tape drives used to store the images in a highly reliable manner. The images are stored in a suitable archival format, such as the above-mentioned DICOM format. The imaging equipment 705 includes any type of equipment to generate images, including medical equipment (e.g., X-ray equipment, CT scanners, and MR scanners).

For this embodiment, the medical informatics system 700 includes at least one image server 720. The pyramidal data structure is stored in image server 720. Image server 720 is coupled to one or more client computers via a direct or network connection, labeled 780 on FIG. 7. The user interface of the present invention operates on client computers. However, the user interface may operate as a server application that provides functionality to the client computers. For the example shown in FIG. 7, client computers include both thick clients (i.e., a computer with robust processing, memory, and display resources), as well as thin clients (i.e., a computer with minimal processing, memory, and display resources). Specifically, for the example embodiment of FIG. 7, a client computer 740 consists of a workstation, client computers 750 and 760 consist of desktop computers, and client computers 770 consist of a portable or notebook computer.

For this embodiment, the image server 720 transmits to the client computers 740, 750 and 760 transformations of the source image 715 ("transform data"), stored as pyramidal data structure 735, to re-create images and sub-images in the client computers. The image server 720 transfers only the coefficient data required to reconstruct a requested image at the client(s), thus implementing a "just in time" data delivery system. The dynamic transfer syntax technique permit use of a network with moderate bandwidth capacity, while still providing low latency for transfer of large data files from the image server 720 to client computers 740, 750, 760 and 770. For example, the network 780 in the medical informatics system 700 may utilize an Ethernet (10baseT) medium or an ISDN transmission medium. Regardless, any network, including wide area networks (WANs) and local area networks (LANs) may be used without deviating from the spirit and scope of the invention. The medical informatics system 700 processes one or more source images 715. Generally, the source image(s) 715 includes a digitized medical image generated from medical instrumentation (e.g., mammogram, X-Ray, MRI, CATSCAN, etc.). Although the present invention is described for use with medical images, any large data file may be used as a source image 115 without deviating from the spirit or scope of the invention.

As shown in FIG. 7, the source image(s) 715 are input to decomposition processing 125. In general, decomposition processing 125 transforms the source images 715 into the dynamic transfer syntax representation, also referred to herein as pyramidal data structure 735. In general, the pyramidal data structure 735 comprises a hierarchical representation of the source image. Each level of the hierarchical representation is sufficient to reconstruct the source image at a given resolution. In one embodiment, the decomposition processing 725 utilizes a sub-band decomposition to generate the hierarchical representation. In general, sub-band decomposition consists of executing a process to separate "high-pass" information from "low-pass" information. For the sub-band decomposition embodiment, decomposition processing 125 comprises a finite impulse response (FIR) filter.

In one embodiment that uses sub-band decomposition, the decomposition processing 125 uses wavelet transforms, which are a sub-class of the sub-band decomposition transform. In general, the wavelet transform may be selected so that the kernels aggregate a sufficient amount of the image information into the terms or coefficients. Specifically, the information is aggregated into the "low low" component of the decomposition. In one embodiment, kernels of the wavelet transform are selected so as to balance the computational efficiency of the transform with optimization of the aggregate information in the low pass components. This characteristic of wavelet transforms permits transfer, and subsequent display, of a good representation of the source image at a particular resolution while maintaining the computational efficiency of the transform.

The wavelet transform function embodiment generates mathematically independent information among the levels of the hierarchical representation. Accordingly, there is no redundant information in the pyramidal data structure 735. Thus, pyramidal data structure 735 is not merely multiple replications of the source image at different resolutions, which consists of redundant information, but it contains unique data at the different levels of the hierarchical representation. The mathematically independent nature of the wavelet transform permits minimizing the amount of data transferred over a network, by requiring only the transfer of "additional data" not yet transferred to the computer from the server necessary to construct a given image. The wavelet transforms are lossless, in that no data from the original source image is lost in the decomposition into the pyramidal data structure 735. Accordingly, the dynamic transfer syntax system has applications for use in medical imaging and medical imaging applications.

In one embodiment, fixed point kernels are used in the wavelet transform (i.e., decomposition processing 725). The use of fixed point kernels generates coefficients for the pyramidal data structure that permit an easy implementation into a standard pixel footprint. The wavelet transform, a spatial transform, generates a dynamic range of the "low low" component that is equal to the dynamic range of the source image. Because of this characteristic, the "low low" component does not contain overshoot or undershoot components. As a result, the use of fixed point kernels is preferred because no normalization process to convert the transformed dynamic range to the pixel dynamic range is required.

For this embodiment, the medical informatics system 700 directly utilizes the transform coefficients as pixels, without re-scaling the coefficients. The range of the high-pass components (i.e., "low high", "high low", and "high high" components) is the range of the input source data plus two bits per coefficient. This characteristic permits mapping of all components (i.e., high and low pass components) to a given pixel footprint.

The use of the wavelet transform to generate the pyramidal data structure provides a scalable solution for transferring different portions of a large data file. When the source image 715 is decomposed into the pyramidal data structure 735, sub-images and sub-resolution images are extracted directly from memory of the image server 720. The image server then transmits only the data, in the form of physical coefficients, required to reconstruct the exact size of the desired image for display at the client. Accordingly, the multi-resolution format is implicit in the pyramidal data structure.

A wavelet transform is a spatial transform. In general, in a spatial transform, the information is aggregated so as to preserve the predictability of the geometry of the source image. For example, using a wavelet transform with fixed point kernels, specific coefficients of the transform data may be identified that contribute to specific geometric features of the source image (i.e., a pre-defined portion of a source image is directly identifiable in the transform data). In another embodiment, the wavelet transforms use floating point kernels.

In other embodiments, the wavelet transform may be used to generate multi-spectral transform data. In general, multi-spectral transform data aggregates multi-components of the source image into a vector for the transform data. Through use of multi-spectral transform data, the wavelet transform may aggregate multi-dimensional data (e.g., two dimensional, three dimensional, etc.) for a source image. For example, multi-dimensional transform data may be used to reconstruct a source image in three dimensions. Also, the multi-spectral transform data may comprise any type of attribute for binding to the source image, such as color variations and/or non-visual components (e.g., infrared components).

In general, to generate the pyramidal data structure 735, the transform is applied across the columns, and then this transform, or a different transform, is applied across the rows. The selection of the transform for decomposition processing 725 is dependent upon the particular characteristics of the pyramidal data structure desired. Each level of the pyramidal data structure is generated by recurring on the low-pass, "low low", of the previous higher level. This recursion continues until a predetermined size is obtained. For example, in one embodiment, the lowest level in the pyramidal data structure for a source image having an aspect ratio of one-to-one consists of a low-pass component of 128×128. However, any granularity of resolution may be generated for use in a pyramidal data structure without deviating from the spirit or scope of the invention. Also, any quadrant may be used in the recursion process with any desired transform.

Figure 8A:
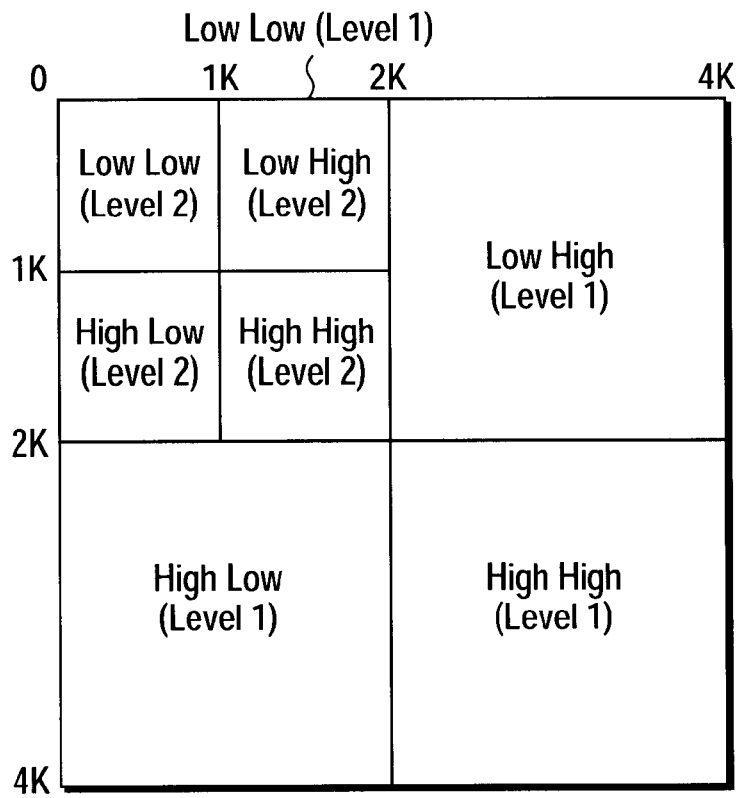
FIG. 8a illustrates an example of a pyramidal data structure.

FIG. 8*a* illustrates an example of a pyramidal data structure. For this example, the source image comprises a 4K×4K image. The decomposition processing 725 generates, in a first iteration, a level one Mallat structure. Specifically, as shown in FIG. 8*a*, a low-pass component, "low low", is generated and consists of a 2K×2K sub-image. The 2K×2K sub-image is labeled in FIG. 8*a* as 805. The high-pass components, consisting of "low high", "high high", and "high low", contain physical coefficient coordinates (e.g., the upper right hand coordinate for the rectangle that constitutes the "low high" component is (4K, 0)).

Figure 8B:
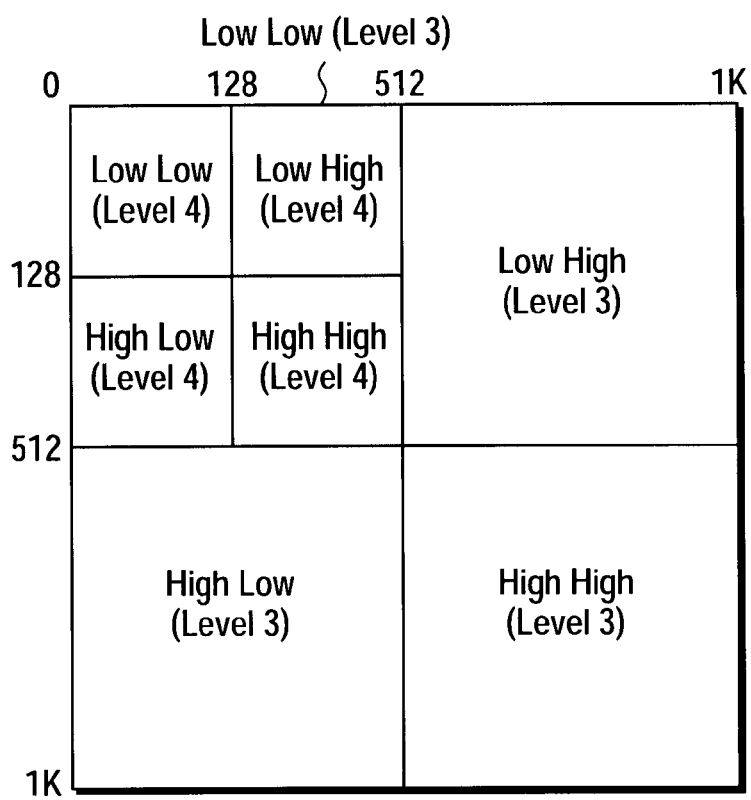

FIG. 8*a* also illustrates a second level decomposition. The second iteration of decomposition processing 725 operates on the low pass (i.e., "low low"), component of the level one data. For the second level, the low-pass component, "low low", consists of a 1K×1K sub-image, as labeled in FIG. 8*a*. FIG. 8*b* illustrates level three and level four decompositions for the 4K×4K source image of FIG. 8*a*. To generate the level three decomposition, decomposition processing 725 operates on the level two "low low" component (i.e., the 1K×1K image). For the level three transform, the low-pass component, "low low", is a 512×512 sub-image as labeled on FIG. 8*a*. FIG. 8*b* also illustrates a fourth level of decomposition for the 4K×4K source image. For the level four transform, the low-pass component comprises a sub-image of 256×256 pixels.

In one embodiment, the wavelet kernel comprises the wavelet kernel derived from D. LeGall and A. Tabatabai, See "Sub-band coding of digital images using symmetric short kernel filters and arithmetic coding techniques," IEEE International Conference on Acoustics, Speech and Signal Processing, New York, N.Y., pp. 761–765, 1988. Any sub-band kernel or pyramid transform could be used within the infrastructure described by the dynamic transfer syntax; however, an integer kernel with no coefficient growth in the low pass term has particular advantages in that the low pass coefficients can be used without processing as pixels, and the transform can be inverted exactly in the integer domain. Although floating point kernels can have superior signal transfer characteristics, the additional processing required to use these coefficients as pixels, and the need for additional storage to guarantee perfect reconstruction works to their disadvantage.

The kernel consists of a low pass and a high pass biorthogonal filter. With input defined as $\{d_j\}$ and $[x]$ defined as the floor function, the forward transform is:

$$\text{Low}[j]=[(d_{2j}+d_{2j+1})/2]$$

$$\text{High}[2]=d_{2j}-d_{2j+1}+\text{Poly}[j]$$

$$\text{Poly}[j]=[(3*\text{Low}[j-2]-22*\text{Low}[j-1]+22*\text{Low}[j+1]-3*\text{Low}[j+2]+32)/64]$$

The inverse transform, used to reconstruct the image, is:

$$d_{2j}=\text{Low}[j]+[(\text{High}[j]-\text{Poly}[j]+1)/2]$$

$$d_{2j+1}=\text{Low}[j]-[(\text{High}[j]-\text{Poly}[j])/2]$$

As discussed above, the wavelet transform is a spatial transform such that the information is aggregated to preserve the predictability of the geometry of the source image. Thus, coefficient coordinates sufficient to reconstruct a desired image or sub-image at a particular level are readily identifiable.

A more complete description of the dynamic transfer syntax is contained in U.S. Provisional Patent Application, entitled "Flexible Representation and Interactive Image Data Delivery Protocol", Serial No. 60/091,697, inventors Paul Joseph Chang and Carlos Bentancourt, filed Jul. 3, 1998, and U.S. patent application, entitled "Methods and Apparatus for Dynamic Transfer of Image Data", Ser. No. 09/339,077, inventors Paul Joseph Chang and Carlos Bentancourt, filed Jun. 23, 1999, both of which are expressly incorporated herein by reference.

Figure 9:
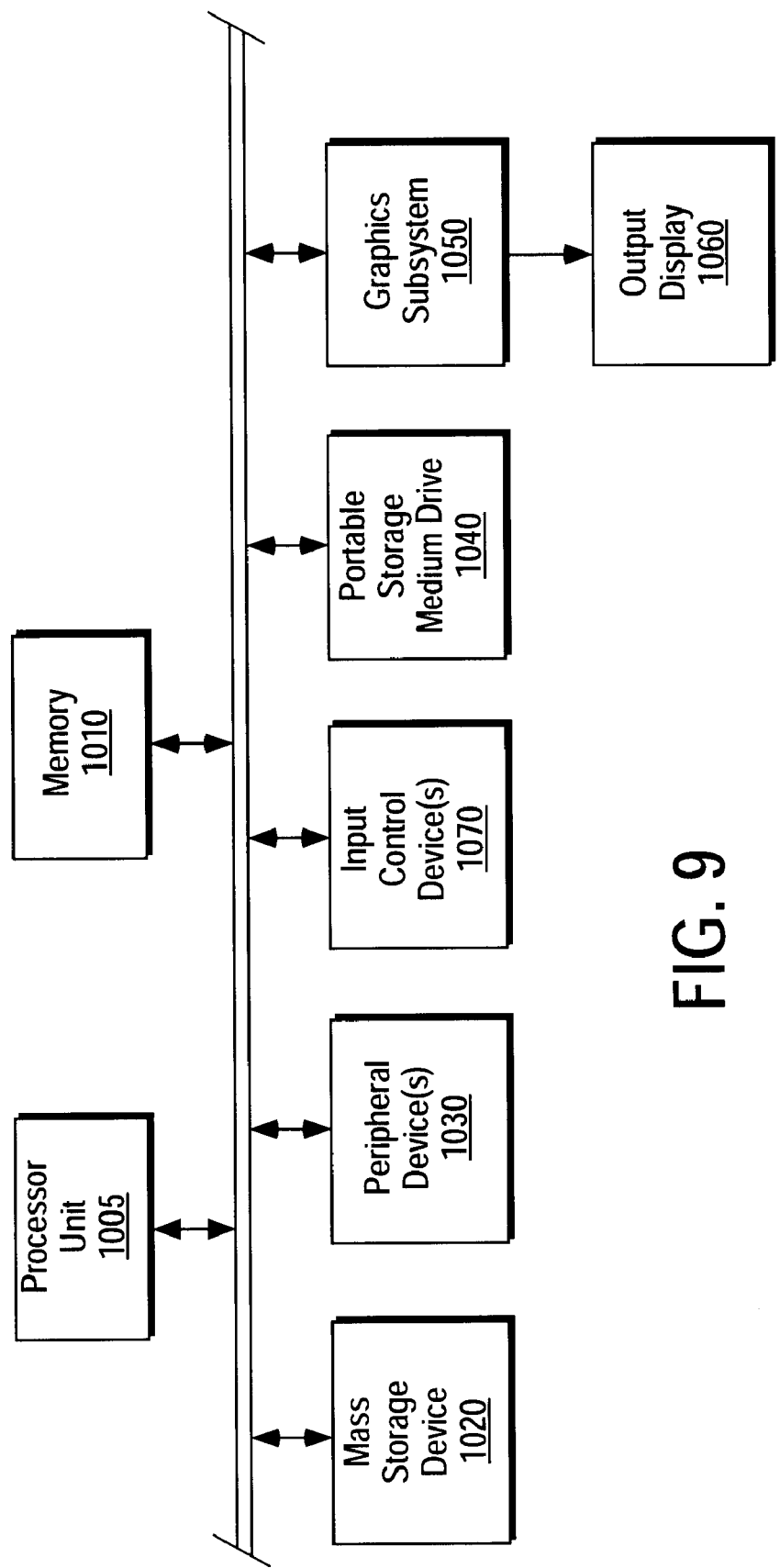
FIG. 9 illustrates a general purpose computer system for implementing the user interface of the invention.

Computer System:

FIG. 9 illustrates a high-level block diagram of a general purpose computer system for implementing the user interface for the medical informatics system. A computer system 1000 contains a processor unit 1005, main memory 1010, and an interconnect bus 1025. The processor unit 1005 may contain a single microprocessor, or may contain a plurality of microprocessors for configuring the computer system 1000 as a multi-processor system. The main memory 1010 stores, in part, instructions and data for execution by the processor unit 1005. If the user interface for the medical informatics system of the present invention is partially implemented in software, the main memory 1010 stores the executable code when in operation. The main memory 1010 may include banks of dynamic random access memory (DRAM) as well as high speed cache memory.

The computer system 1000 further includes a mass storage device 1020, peripheral device(s) 1030, portable storage medium drive(s) 1040, input control device(s) 1070, a graphics subsystem 1050, and an output display 1060. For purposes of simplicity, all components in the computer system 1000 are shown in FIG. 9 as being connected via the bus 1025. However, the computer system 1000 may be connected through one or more data transport means. For example, the processor unit 1005 and the main memory 1010 may be connected via a local microprocessor bus, and the mass storage device 1020, peripheral device(s) 1030, portable storage medium drive(s) 1040, graphics subsystem 1050 may be connected via one or more input/output (I/O) busses. The mass storage device 1020, which may be implemented with a magnetic disk drive or an optical disk drive, is a non-volatile storage device for storing data and instructions for use by the processor unit 1005. In the software embodiment, the mass storage device 1020 stores the user interface software for loading to the main memory 1010.

The portable storage medium drive 1040 operates in conjunction with a portable non-volatile storage medium, such as a floppy disk or a compact disc read only memory (CD-ROM), to input and output data and code to and from the computer system 1000. In one embodiment, the user interface for the medical informatics system software is stored on such a portable medium, and is input to the computer system 1000 via the portable storage medium drive 1040. The peripheral device(s) 1030 may include any type of computer support device, such as an input/output (I/O) interface, to add additional functionality to the computer system 1000. For example, the peripheral device(s) 1030 may include a network interface card for interfacing the computer system 1000 to a network.

The input control device(s) 1070 provide a portion of the user interface for a user of the computer system 1000. The input control device(s) 1070 may include an alphanumeric keypad for inputting alphanumeric and other key information, a cursor control device, such as a mouse, a trackball, stylus, or cursor direction keys. In order to display textual and graphical information, the computer system 1000 contains the graphics subsystem 1050 and the output display 1060. The output display 1060 may include a cathode ray tube (CRT) display or liquid crystal display (LCD). The graphics subsystem 1050 receives textual and graphical information, and processes the information for output to the output display 1060. The components contained in the computer system 1000 are those typically found in general purpose computer systems, and in fact, these components are intended to represent a broad category of such computer components that are well known in the art.

The user interface for the medical informatics system may be implemented in either hardware or software. For the software implementation, the user interface is software that includes a plurality of computer executable instructions for implementation on a general purpose computer system. Prior to loading into a general-purpose computer system, the user interface software may reside as encoded information on a computer readable medium, such as a magnetic floppy disk, magnetic tape, and compact disc read only memory (CD-ROM). In one hardware implementation, the user interface system may comprise a dedicated processor including processor instructions for performing the functions described herein. Circuits may also be developed to perform the functions described herein.

Although the present invention has been described in terms of specific exemplary embodiments, it will be appreciated that various modifications and alterations might be made by those skilled in the art without departing from the spirit and scope of the invention.

What is claimed is:

1. A method for viewing medical images in a computer system, said method comprising the steps of:

receiving, in said computer, graphical identifications for a plurality of studies corresponding to a patient, wherein a study comprises a plurality of related images acquired for said patient, and wherein a graphical identification to an image comprises a thumbnail view of said image;

displaying, on an output display of said computer, a first study in a first horizontal rack, said thumbnail views of said images for said first study being arranged in an adjacent manner within said first horizontal rack;

displaying, on said output display of said computer, a second study in a second horizontal rack, said thumbnail views of said images of said second study being arranged in an adjacent manner within said second horizontal rack, wherein said first and second horizontal racks being vertically deposed on said output display;

providing, through said computer, a means for a user to navigate said images, including panning and zooming said images; and providing, through said computer, a means for a user to reposition said images on said output display.

2. The method as set forth in claim 1, further comprising the step of providing through said computer a means to select said at least two studies of a patient.

3. The method as set forth in claim 2, wherein the step of selecting at least one study of a patient comprises the step of displaying a patient browser view, said patient browser view providing a means to select at least one patient and at least two studies for said patient.

4. The method as set forth in claim 1, wherein the step of providing a means for a user to reposition said images comprises the step of providing to a user a means to vertically re-arrange an order of display for said studies.

5. The method as set forth in claim 1, wherein the step of providing a means for a user to reposition said images comprises the step of providing to a user a means to scroll horizontally among said medical images/series of a study.

6. The method as set forth in claim 1, wherein the step of providing a means for a user to reposition said images comprises the step of providing to a user a means to re-arrange an order of display for said medical images/series within a study.

7. The method as set forth in claim 1, wherein the step of providing a means for a user to navigate said images comprises the step of providing to a user a means to resize said medical images.

8. The method as set forth in claim 7, wherein the step of providing to a user a means to resize said medical images further comprises the step of maintaining an aspect ratio between height and width of said medical image.

9. The method as set forth in claim 1, wherein the step of providing a means for a user to navigate said images comprises the step of providing to a user a means to pan a medical image to display a different portion of a medical image.

10. The method as set forth in claim 1, wherein the step of providing a means for a user to navigate said images comprises the step of providing to a user a means to zoom in on a portion of a medical image to view said image at a different resolution.

11. The method as set forth in claim 1, further comprising the step of providing to a user a means to horizontally scroll said medical images within a study.

12. The method as set forth in claim 1, further comprising the steps of:

receiving at least two series for a study; and linking said two series so as to provide simultaneous cine.

13. The method as set forth in claim 1, further comprising the step of displaying, in response to user selection, a report associated with said study.

14. A computer readable medium comprising a plurality of instructions, which when executed by a computer, causes the computer to perform the steps of:

receiving, in said computer, graphical identifications for a plurality of studies corresponding to a patient, wherein a study comprises a plurality of related images acquired for said patient, and wherein a graphical identification to an image comprises a thumbnail view of said image;

displaying, on an output display of said computer, a first study in a first horizontal rack, said thumbnail views of said images for said first study being arranged in an adjacent manner within said first horizontal rack;

displaying, on said output display of said computer, a second study in a second horizontal rack, said thumbnail views of said images of said second study being arranged in an adjacent manner within said second horizontal rack, wherein said first and second horizontal racks being vertically deposed on said output display;

providing, through said computer, a means for a user to navigate said images, including panning and zooming said images; and providing, through said computer, a means for a user to reposition said images on said output display.

15. The computer readable medium as set forth in claim 14, further comprising the step of providing through said computer a means to select said at least two studies of a patient.

16. The computer readable medium as set forth in claim 15, wherein the step of selecting at least one study of a patient comprises the step of displaying a patient browser view, said patient browser view providing a means to select at least one patient and at least two studies for said patient.

17. The computer readable medium as set forth in claim 14, wherein the step of providing a means for a user to reposition said images comprises the step of providing to a user a means to vertically re-arrange an order of display for said studies.

18. The computer readable medium as set forth in claim 14, wherein the step of providing a means for a user to reposition said images comprises the step of providing to a user a means to scroll horizontally among said medical images/series of a study.

19. The computer readable medium as set forth in claim 14, wherein the step of providing a means for a user to reposition said images comprises the step of providing to a user a means to re-arrange an order of display for said medical images/series within a study.

20. The computer readable medium as set forth in claim 14, wherein the step of providing a means for a user to navigate said images comprises the step of providing to a user a means to resize said medical images.

21. The computer readable medium as set forth in claim 20, wherein the step of providing to a user a means to resize said medical images further comprises the step of maintaining an aspect ratio between height and width of said medical image.

22. The computer readable medium as set forth in claim 14, wherein the step of providing a means for a user to navigate said images comprises the step of providing to a user a means to pan a medical image to display a different portion of a medical image.

23. The computer readable medium as set forth in claim 14, the step of providing a means for a user to navigate said images comprises the step of providing to a user a means to zoom in on a portion of a medical image to view said image at a different resolution.

24. The computer readable medium as set forth in claim 14, further comprising the step of providing to a user a means to horizontally scroll said medical images within a study.

25. The computer readable medium as set forth in claim 14, further comprising the steps of:

receiving at least two series for a study; and linking said two series so as to provide simultaneous cine.

26. The computer readable medium as set forth in claim 14, further comprising the step of displaying, in response to user selection, a report associated with said study.

27. A computer system comprising:

input device for receiving graphical identifications for a plurality of studies corresponding to a patient, wherein a study comprises a plurality of related images acquired for said patient, and wherein a graphical identification to an image comprises a thumbnail view of said image;

output display for displaying a first study in a first horizontal rack, said thumbnail views of said images for said first study being arranged in an adjacent manner within said first horizontal rack, and for displaying a second study in a second horizontal rack, said thumbnail views of said images of said second study being arranged in an adjacent manner within said second horizontal rack, wherein said first and second horizontal racks being vertically deposed on said output display;

input control device for receiving user input; and processing unit, coupled to said input control device, for providing a means for a user to reposition said images on said output, and for providing a means for a user to navigate said images, including panning and zooming said images.

* * * * *